United States Patent [19]

Cordey

[11] 4,359,906
[45] Nov. 23, 1982

[54] DEVICE AND METHOD FOR INSERTING A BONE SCREW

[75] Inventor: Jacque R. Cordey, Davos, Switzerland

[73] Assignee: Synthes AG, Grabenstrasse, Switzerland

[21] Appl. No.: 40,099

[22] Filed: May 18, 1979

[30] Foreign Application Priority Data

May 20, 1978 [CH] Switzerland ............... 5460/78
Dec. 13, 1978 [DE] Fed. Rep. of Germany ....... 2853869

[51] Int. Cl.³ .............. B25B 23/14; G01L 5/24
[52] U.S. Cl. .................. 73/862.23; 73/761; 81/467
[58] Field of Search ............... 73/761, 862.23, 862.24; 173/12, 1; 81/467; 29/407

[56] References Cited

U.S. PATENT DOCUMENTS 3,974,883  8/1976  Sigmund ................... 173/12
4,161,220  7/1979  Carlin et al. ............. 173/1
4,305,471 12/1981  Eshghy .................... 173/12

OTHER PUBLICATIONS

S. M. Perren, et al. –"Die Mechanik der Plattenstellschraube"–Unfallheilkunde–Apr. 1978.

*Primary Examiner*—Charles A. Ruehl
*Attorney, Agent, or Firm*—Davis, Hoxie, Faithfull & Hapgood

[57] ABSTRACT

A device for tightening a screw into bone material to a defined torque value $M_O$ less than that at which the bone irreversibly deforms including means for measuring the torque, M, necessary to obtain an angular rotation, $\alpha$, measured from the point where the screw first contacts the underlying material, and determining a value for $M_O$ as a function of $M/\alpha$.

3 Claims, 5 Drawing Figures

DEVICE AND METHOD FOR INSERTING A BONE SCREW

BACKGROUND OF THE INVENTION

The present invention relates to a device for tightening a bone screw into bone material during orthopedic or traumatologic surgery to a torque value $M_o$ which is less, by a predetermined fixed factor, than the torque value at which the bone material irreversibly deforms.

In orthopedic and traumatologic surgery, particularly those in the case of fractures, bone fragments to be joined are often fixed together by means of bone screws or bone implants in conjunction with such screws. A bone screw should be tightened to such an extend that on the one hand the bone fragments are pressed together as tightly as possible and on the other hand the bone fragments, the screw and the respective threads in the bone and on the screw are not damaged. A screw should therefore be tightened until the tightening torque has reached an optimum value slightly below that at which the threads are stripped.

Current practice is for surgeons to tighten the screws by feel. There have already been tests carried out to determine the torque values occurring, in which the surgeons have used a screwdriver with a torque measuring transducer. The results of these tests have been published in the paper "Dosierung des Drehmoments beim Einsetzen von Knochenschrauben" ("Dosage of Torque for the Insertion of Bone Screws") by J. Cordey, W. Widmer, A. Rohner and S. M. Perren in 115 *Zeitschrift fur Orthopadie und ihre Grenzgebiete* ("Journal of Orthopaedics and Allied Fields"), pp. 601&602 (1977.)

For surgeons who do not yet have much experience it is difficult to tighten the screws by feel just enough for the torque obtained at the end of tightening to be approximately equal to the optimum value. The surgeons could naturally use a screwdriver which limits the tightening torque for the screws to a pre-set definite maximum value. This would not be practical, however, since the various torque values at which the threads are stripped depend on the individual features of the bone and vary considerably from case to case, from bone to bone in the same individual and from location to location in the same bone. Tests in which screws with a diameter of 4.5 mm were screwed into the tibiae of fifteen different human cadavers have shown that the torque value at which the threads are stripped vary between about 1 and 7 Newton meters. If the torque were limited to a fixed value, this value would therefore have to be such that the threads would not be stripped even in the case of the bones with the lowest strength. This would then mean that when screws are inserted into bones of greater strength the torque would be far below the optimum for that bone.

SUMMARY OF THE INVENTION

It is an object of the present invention to provide a device permitting the surgeon to tighten bone screws in bones of differing strength which approaches the optimum torque value in each case.

This and other objects are provided by a bone screw driving device adapted for use in orthopedic and traumatolgic surgery for tightening a bone screw into bone material to a defined torque value $M_o$ which is less than the torque value at which said bone material irreversibly deforms, said device comprising screw driving means for engaging said bone screw to rotate and apply tightening torque to said bone screw, means for measuring the amount of tightening torque applied to said bone screw by said screw driving means, means for measuring the angle of rotation of said bone screw, and control means for relating the tightening torque applied to said bone screw commencing with the contact of the screw head with the underlying material, such as bone material or an implant, and the angle of rotation of said bone screw commencing with said contact, specifying a torque value $M_o$ which is less, by a predetermined fixed factor, than the torque value at which said bone material irreversibly deforms and monitoring the instantaneous tightening torque value for the presence of said torque value $M_o$. Said device may also include means for indicating the presence of said torque value $M_o$ or means for disengaging the application of tightening torque on instantaneous torque reaching said torque value $M_o$.

BRIEF DESCRIPTION OF THE DRAWING

As an aid in understanding the invention disclosed, reference may be made to the following description of its preferred embodiments taken in conjunction with the figures of the accompanying drawing in which.

DESCRIPTION OF THE PREFERRED EMBODIMENT

The present invention is based on the finding obtained in the previously mentioned tests with tibiae that the torque values at which the threads are stripped can be calculated in advance with a high degree of accuracy from the increases in torque and in angle of rotation as the screw is tightened. If the first derivative of the torque is determined with respect to the angle of rotation or if the zero point of the angle of rotation is suitably established and the ratio of torque to angle of rotation is determined commencing at that point in the screwing-in process at which the head of the screw rests on the bone or on a bone plate (which might still be present), there is a close connection between the torque at which irreversible deformation occur (such as the thread being stripped) and the quantities mentioned. In other words, the torque at which the thread is stripped can be calculated in advance for all bones as a close approximation by forming a quantity which is dependent in a fixed relationship on the derivative of the torque with respect to the angle of rotation or on the ratio of torque to angle of rotation.

Figure 1:
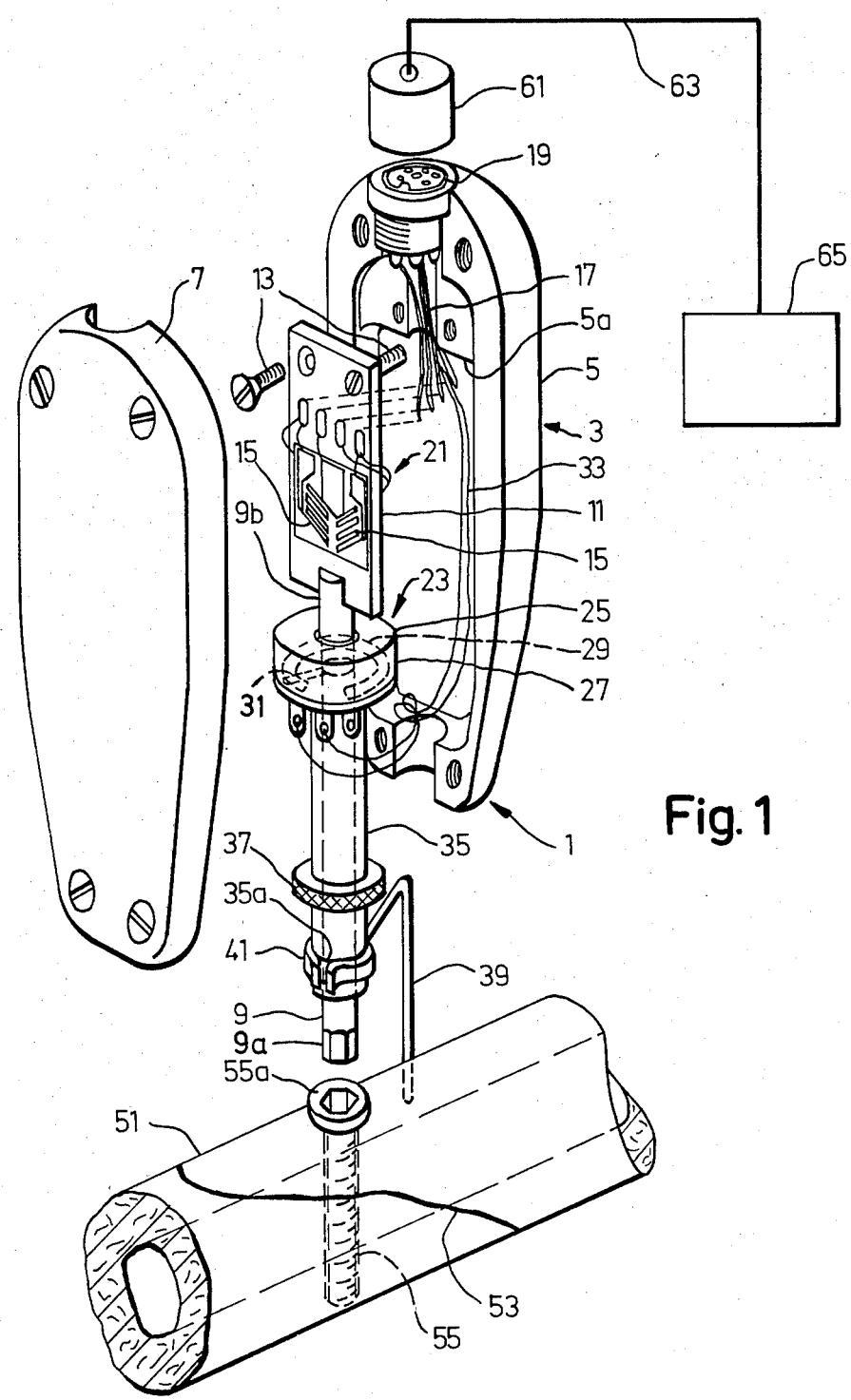
FIG. 1 illustrates a device in accordance with the present invention, such as a screwdriver, in axonometric projection for screwing a bone screw into a bone, the handle of the screwdriver being shown in its partially dismantled state.

As shown in FIG. 1, the device comprises a tool, namely a screwdriver 1, which is provided with a holder 3 which serves as a handle, comprising two parts 5 and 7 which are screwed together. The screwdriver has, in addition, a shank 9, the free end 9a of which, projecting from the holder 3, is in the form of a hexagonal tip or lug. The other end 9b of the shank 9 is provided with a slot at right-angles to the shaft. One end of a torsion member 11 projects into this slot and is positively connected with the shank 9 there. The torsion member 11 comprises a small, elongated metal plate which can be distorted under an elastic deformation. The end of the torsion member 11 opposite to the shank 9 rests on a shoulder 5a of the handle part 5 and is secured there by means of screws 13. Two strain gauges 15 are attached to each side of the torsion member 11, such as by gluing, in such an orientation that the two strain gauges 15 on the same side of the torsion member form an angle of 90 degrees with respect to each other, this angle being bisected by a plane through the axis of the shank. The strain gauges 15 are connected via leads 17 with the connections of a socket 19 secured to the holder 3. The holder 3 is provided with a cavity in which the torsion member 11 can turn without hindrance. As will be described in greater detail later, the torsion member 11 and its associated strain gauges 15 together form a torque measuring device, or a torque measuring transducer 21. In addition, the screwdriver 1 is provided with an angle of rotation measuring device, or an angle of rotation measuring transducer 23. The latter has a potentiometer 25 with a casing 27. An annular resistor element 29 is rigidly secured to the inside of the potentiometer casing 27. On the shaft of the potentiometer, which is formed by a section of shank 9, a sliding contact 31 is positively mounted. Two terminals of the potentiometer are connected to contacts in the socket 19 by flexible leads 33. The casing 27 of potentiometer 25 is positively connected with a sleeve 35 which coaxially encloses the shank 9 and can be turned in relation to this. The sleeve 35 passes through an aperture in the handle 3, in which it is arranged to rotate in a bearing. The cavity in the holder 3 is designed and the leads 33 are arranged in such a way that the sleeve 35 together with the potentiometer casing 27 can turn through almost a complete revolution around the shank 9. A knurled adjusting ring 37 is positively mounted on the sleeve 35. Near the end of the sleeve 35 remote from the holder 3, the sleeve is provided with an annular groove 35a. A stop 39 formed by an angled rod is secured to the sleeve 35 by a spring clip 41 engaging in the groove 35a. The spring tension of clip 41 is such that the stop 39 can secure the sleeve 35 positively against rotation while the sleeve can still be turned manually against the stop when desired. The clip 41 permits the stop 39 to be clipped on and off the sleeve 35 from the side.

FIG. 1 also shows a bone 51, such as for example a human tibia. The bone 51 is broken into two pieces or fragments which contact each other on a fracture surface 53. The two pieces of bone are held together by means of at least one bone screw 55, the head 55a of which has a hexagonal socket.

Figure 2:
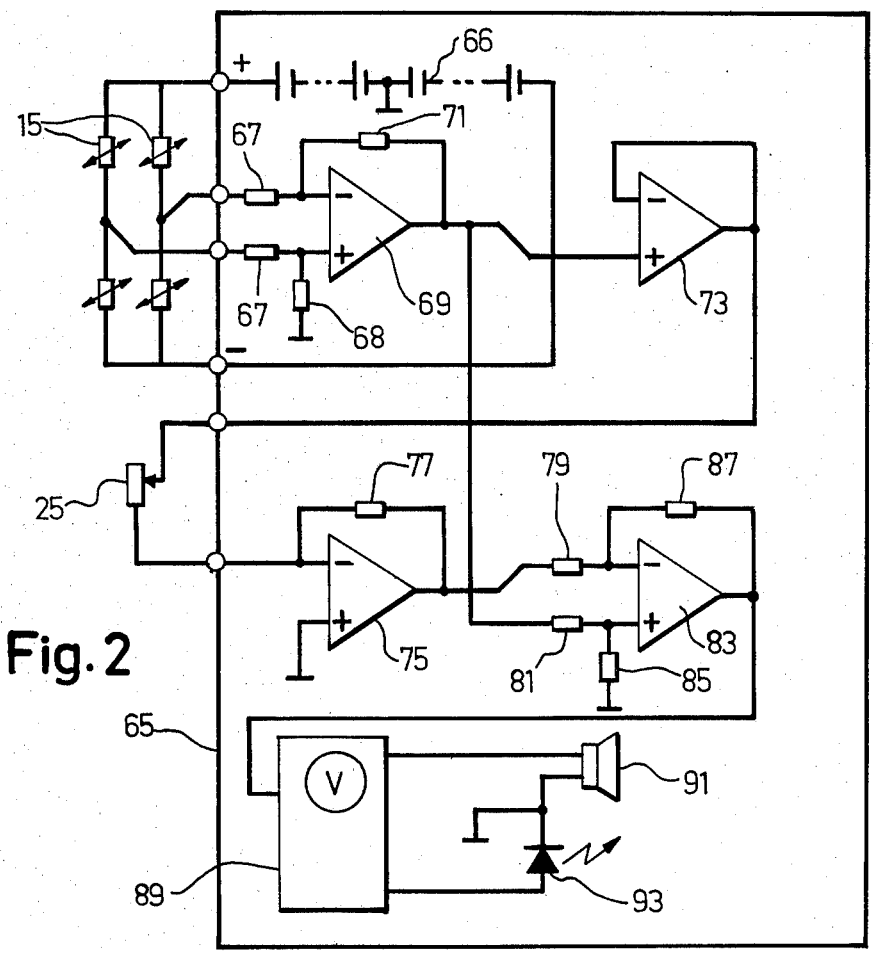
FIG. 2 is a circuit diagram of the basic electronic section which can be connected to the screwdriver.

The socket 19 is connected by means of a plug 61 and a cable 63 with an electronic section, or circuit, 65, the basic circuit diagram of which is shown in simplified form in FIG. 2. The four strain gauges 15 of the torque measuring device 21 together form a bridge circuit. Two of the four terminals of the bridge circuit are connected with the positive and negative poles respectively of a d.c. voltage source 66. The two other terminals of the bridge circuit are connected via one resistor 67 each with the inverting and non-inverting inputs respectively of an operational amplifier 69. The inverting input of the amplifier 69 is connected via a feedback resistor 71 to the amplifier output and the non-inverting input is connected via a resistor 68 to the electrical earth, or ground, connection. The output of the amplifier 69 is connected to the non-inverting input of an operational amplifier 73, the inverting input of which is directly connected to the amplifier output and which serves as an impedance converter. The output of the amplifier 73 is connected via the variable resistance length of the potentiometer 25 to the inverting input of an operational amplifier 75, the inverting input and the output of which are connected by a feedback resistor 77 and the non-inverting input of which is electrically connected to ground. The output of the amplifier 75 is connected via a resistor 79 to the inverting input of an operational amplifier 83, the inverting input of which in addition is connected via a feedback resistor 87 to the amplifier output. The non-inverting input of the amplifier 83 is connected on the one hand via a resistor 81 to the output of the amplifier 69 and on the other hand to electrical ground via a resistor 85. The two resistors 79 and 81 are of equal size, as are the two resistors 85 and 87. The amplifier 83 thus forms a subtraction circuit which supplies an output voltage proportional to the difference between the output voltages of amplifiers 69 and 75. The output of the amplifier 83 is connected to the input of a level monitor 89, the outputs of which are connected to an acoustic signal generator 91, such as a loud-speaker, and an optical signal generator 93, such as a light-emitting diode or a flashing lamp.

Figure 3:
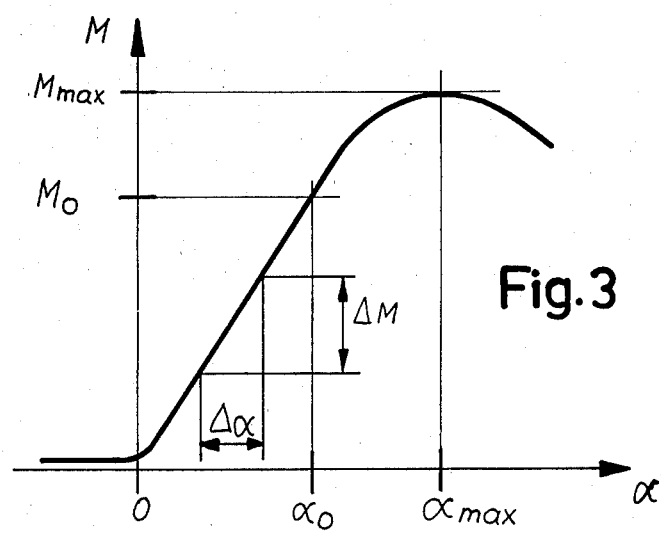
FIG. 3 is a graph of a curve illustrating the dependence of torque on the angle of rotation.

FIG. 3 illustrates the dependence of the torque M required for inserting a screw 55 into a bone 51 on the angle of rotation $\alpha$. The angle of rotation is measured from that position of the screw where its head 55a has just come into contact with the bone 51. The angle of rotation $\alpha$ is measured positively in the direction of rotation in which the screw is screwed in.

Before the bone screw 55 is inserted into the bone 51, the bone is provided with an appropriate tapped hole which may be countersunk for the screw head. The screw 55 is then screwed into this tapped hole until the screw head comes into contact with the bone. During this part of the process of inserting the screw, i.e., before the screw head touches the bone, only a relatively small torque is necessary for screwing in the screw. With screws 4.5 mm in diameter used for the tests, the maximum torque required in this part of the process was only about 0.5 Newton meters. As soon as the head of the bone screw lies on the bone, i.e., at the point where the angle of rotation $\alpha$ has, by definition, the value zero, the torque M increases sharply as the screw is tightened. As can be seen in FIG. 3, over a certain range of angle the torque M increases approximately in linear fashion with the angle of rotation $\alpha$. If the screw is tightened even further, the bone material begins to undergo plastic deformation and the increase in torque drops. At an angle of rotation termed $\alpha_{max}$ the torque then reaches a maximum value $M_{max}$ and decreases as the screw is tightened further until finally the thread of the screw is stripped from the bone or the bone or screw is otherwise damaged.

As has already been mentioned at the beginning, tests in which screws 4.5 mm in diameter from the Swiss Association for the Study of Osteosynthesis were screwed into the tibiae of fifteen different human cadavers have shown that the maximum torque value $M_{max}$ varies between bones of different individuals in the range from about 1 to 7 Newton meters. It was, however, recognised that the maximum torque $M_{max}$ is as a first approximation proportional to the value of the first derivative of the torque with respect to the angle of rotation in that part of the curve which is rising in approximately linear fashion. As a first approximation, therefore, it follows that $$M_{max} \simeq k \partial M/\partial \alpha \qquad (1)$$

where k is a constant which applies to all bones of equal or different strength. If the angle $\alpha$ is measured in radian measure, then k has a value of about 1.3 for the screws in question.

Since in the range in which the derivative $\partial M/\partial \alpha$ is to be measured, the curve in FIG. 3 rises in approximately linear fashion, the differential variations $\partial M/\partial \alpha$ can be substituted as a close approximation by differences $\Delta M/\Delta \alpha$ of finite size. The first derivative can even as a close approximation be substituted by the quotient $M/\alpha$. If M and $\alpha$ are measured in the approximately linear section of the curve, the following relations are found to hold true as a first approximation:

$$M_{max} \simeq k \Delta M/\Delta \alpha \qquad (2)$$

$$M_{max} \simeq k M/\alpha \qquad (3)$$

When the screws are used in surgery involving bone they should be tightened only as long as there is no irreversible deformation of the bone material and of course also no irreversible deformation of the screw material. An admissible or optimum torque is therefore defined the value $M_o$, which is smaller than $M_{max}$. The optimum torque can thus be determined by making it smaller by a fixed, constant safety factor s than the maximum value M defined in one of the formulae (1) to (3). This constant safety factor s naturally has a value which is smaller than 1 and might, for example, be 0.7. The optimum torque $M_o$ can therefore, using formulae (1) to (3), have one of the following values:

$$M_o = sk \partial M/\partial \alpha \qquad (4)$$

$$M_o = sk \Delta M/\Delta \alpha \qquad (5)$$

$$M_o = sk M/\alpha \qquad (6)$$

The tests on tibiae mentioned earlier show however, that it is useful to add another constant to the right-hand side of formulae (4) to (6). The behavior is even more favourable if another summand is added which is proportional to $(\partial M/\partial \alpha)^2$ or $(\Delta M/\Delta \alpha)^2$ or $(M/\alpha)^2$, respectively. The optimum value $M_o$ can then be expressed by one of the following formulae:

$$M_o = c_0 + c_1 \partial M/\partial \alpha + (\partial M/\partial \alpha)^2 \qquad (7)$$

$$M_o = c_0 + c_1 \Delta M/\Delta \alpha + c_2 (\Delta M/\Delta \alpha)^2 \qquad (8)$$

$$M_o = c_0 + c_1 M/\alpha + c_2 (M/\alpha)^2 \qquad (9)$$

Here $c_0$, $c_1$ and $c_2$ are constants. Depending on the accuracy of optimisation aimed at, all three terms on the right-hand side of formulae (7), (8) and (9) can be taken into account or the third terms and possibly the first terms as well can be omitted, i.e., the constants $c_2$ and $c_0$, respectively can be made equal to zero.

Figure 4:
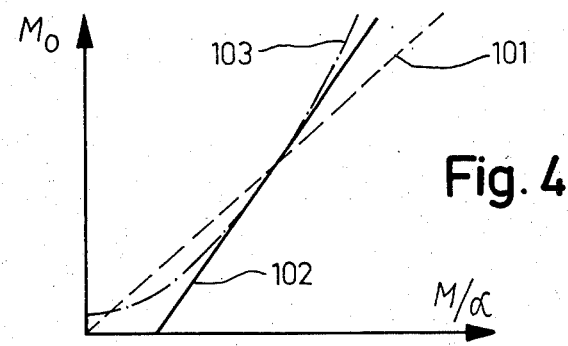
FIG. 4 is a graph of several curves illustrating the dependence of optimum torque $M_o$ on the ratio $M/\alpha$.

FIG. 4 shows the dependence of the optimum value $M_o$ on the ratio $M/\alpha$ for three different possible cases. The straight line 101 holds true for the case where only the constant $c_1$ has a value other than zero. The straight line 102 shows the dependence of $M_o$ for the case where, in addition to constant $c_1$, the constant $c_0$ also has a value other than zero. The curve 103 finally applies to the case where all three constants $c_0$, $c_1$ and $c_2$ have values other than zero. The constant will naturally have different values depending on whether the constants $c_0$ and $c_2$ are equal to or not equal to zero. The constants chosen are such that the optimum values $M_o$ determined by the straight lines 101 or 102 or by the curve 103 are smaller than the maximum values $M_{max}$ measured with the relevant ration $M/\alpha$.

A relationship between the ratio $M/\alpha$ and the optimum value $M_o$ corresponding to the straight line 101 can be realised by means of the basis circuit of the electronic section 65 shown in FIG. 2. A relationship in accordance with the straight line 102 or the curve 103 can be produced by means of a minor addition to the basic circuit of the electronic section, as will be explained below. Before that, however, the way in which a bone screw 55 is screwed into the bone 51 and the way in which the basic version of the electronic section 65 functions will now be described.

If, then, the bone screw 55 is to be screwed into the tapped hole in the bone 51, it can be screwed in initially by means of a previously known manual or pneumatically driven screwdriver or possibly even using the screwdriver 1 with the stop 39 removed from the sleeve 35 for this purpose, until the screw head 55a comes into contact with the bone 51. Further tightening of the screw should then be effected only with the screwdriver 1 of the present invention with the stop 39 fitted into place.

The angle of rotation at which the screw head touches the bone or implant (and where $\alpha$, by definition, has the value zero) can be ascertained without any difficulty by the surgeon because it is then that the torque required to turn the screw increases abruptly. Moreover, the surgeon can also of course visually check the position of the screw head.

Now that the screw 55 is in this position and the end 9a of the screwdriver shank 9 is inserted in the socket in the screw head 55a, the stop 39 must first of all be brought to rest against the bone and the potentiometer 25 must be moved to the intended starting position, i.e., the resistance value of the potentiometer must be set to zero. Since the screw 55, for example, has a right-hand thread, the stop 39 must be brought into a position where it rests against the bone in such a way as to prevent the sleeve 35 from being rotated in a clockwise direction. The surgeon now holds the stop 39 firmly in this position and turns the sleeve 35 by means of the adjusting ring 37 in a clockwise direction viewed from the holder 3 until the start of the resistor 29 reaches the sliding contact 31. The potentiometer is fitted with a stop which makes it possible to set it to this position without any difficulty.

Once the potentiometer has thus been placed in the correct starting position, the surgeon can tighten the screw 55 by turning the holder 3 clockwise. The resistance of the potentiometer then increases in proportion to the angle of rotation $\alpha$. In addition, the torsion member 11 is distorted in proportion to the torque M transmitted by the shank 9. Hence voltages are applied to the inputs of the amplifier 69, the difference between which is proportional to the torque M.

The electronic section 65 is designed so that the output voltages of the amplifiers 69 and 73 are proportional to the torque M. The feedback resistor 77 is tuned in such a way to the resistance of the potentiometer 25 that the output voltage of the amplifier 75 is equal to the value of the output voltage of the amplifiers 69 and 73 multiplied by the factor $c_1/\alpha$. The amplifier 83 then supplies an output voltage which is proportional to the difference $M - M_o$. The level monitor 89 is so designed that it sends an electrical signal to the signal generators 91 and 93 when the instantaneous torque becomes equal to or greater than $M_o$. The signal generators then generate an acoustic signal, for example a buzzing tone, and an optical signal which tells the surgeon that the torque has reached the defined torque value $M_o$. The surgeon can then withdraw the end of the shank 9a from the socket in the screw head.

Figure 5:
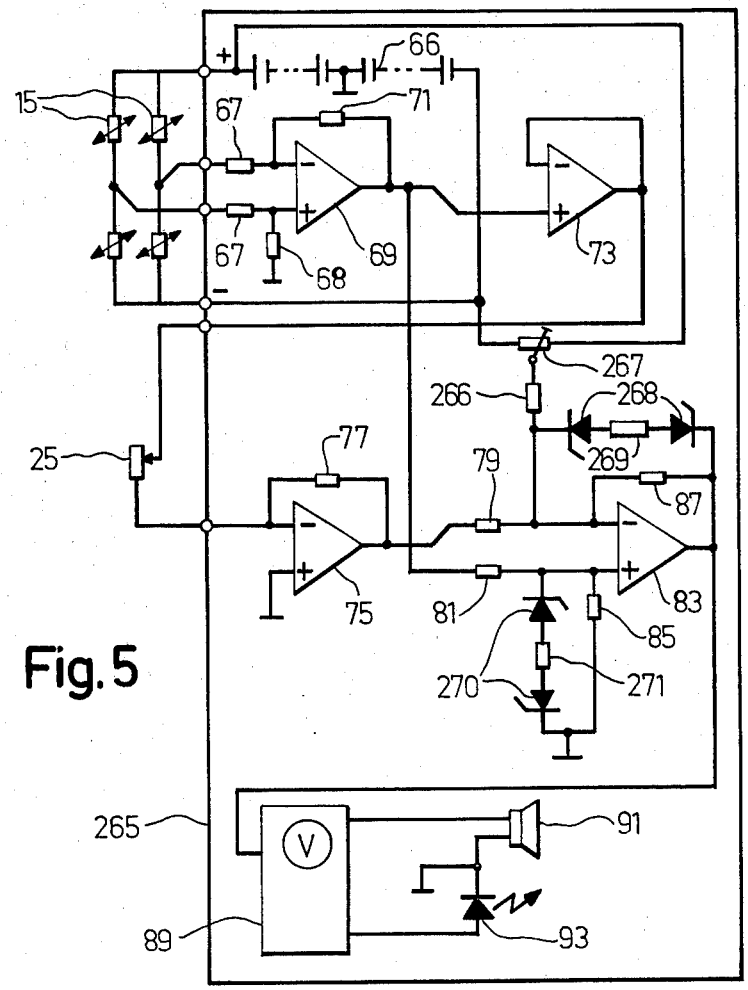
FIG. 5 is a variant of the basic electronic circuit diagram shown in FIG. 2.

FIG. 5 shows the circuit diagram of a variant design of an electronic section 265 which makes it possible to reproduce the dependence illustrated by curve 103 in FIG. 4 of the optimum torque value $M_o$ on the ratio $M/\alpha$. The electronic section 265 contains all the components present in the electronic section 65 plus a few additional components for the amplifier stage containing the amplifier 83. The inverting input of the amplifier 83 of the electronic section 265 is also connected via a resistor 266 to the center tap of a trimming potentiometer 267, the two other terminals of which are connected directly or via a resistor with the two poles of the d.c. voltage source 66. The inverting input of the amplifier 83 of the electronic section 265 is connected via two parallel-connected negative feedback arms to the output of the amplifier 83, i.e., via the resistor 87 already present in the electronic section 65 and in addition via the two opposed polarity Zener diodes 268 and the resistor 269 connected in series with them. The non-inverting input of the amplifier 83 of the electronic section 265 is connected to earth via two parallel-connected arms, i.e., on the one hand via the resistor 85 and on the other hand via to two opposed polarity Zener diodes 270 and the resistor 271 connected in series with them.

A d.c. voltage different from the ground potential is taken to the inverting input of the amplifier 83 via the trimming potentiometer 267 (which forms a voltage divider) and the resistor 266. By appropriate selection of the resistances of the resistor 266 and the trimming potentiometer 267, the value of the constant $c_0$ can be determined. The values of the resistors 79, 81, 85 and 87 determine the value of the constant $c_1$. The components 268, 269, 270, 271 show a dependence on the ratio $M/\alpha$ which is at least approximately quadratic and thus determine the value of the constant $c_2$.

If, of the constants $c_0$, $c_1$ and $c_2$ in equations (7), (8) and (9), only the constants $c_0$ and $c_1$ are to be other than zero the Zener diodes 268 and 270 and the resistors 269 and 271 can be omitted. Conversely, if only the constants $C_1$ and $C_2$ are to be other than zero the resistor 266 and the trimming potentiometer 267 can be omitted.

Judging by the results of the tests carried out, the optimum value $M_o$ can generally be set with sufficient accuracy if its dependence on the ratio $M/\alpha$ is established by a straight line of the type of straight line 102 in FIG. 4. In a special version of the device according to the invention, therefore, the constants $c_0$ and $c_1$ are made unequal to zero and the constant $c_2$ equal to zero. Accordingly the two Zener diodes 268 in the electronic section 265 and the resistor 269 can be omitted.

Once the screw head has come into contact with the surface of the bone, the screws only have to be turned through part of a full circle, which means that a potentiometer 29 which permits almost a full revolution is sufficient for measuring the angle of rotation.

The device shown in FIG. 1 thus enables a surgeon to tighten screws in bones to such an extent that the torque at the end of the tightening process is approximately equal to the optimum torque value $M_o$ in each case even when the bone quality differs, this optimum torque value $M_o$ being equal to a maximum value $M_{max}$ at which the thread would be stripped multiplied by a predetermined safety factor. In this way the pieces of the broken bone can be joined together with approximately the maximum possible compressive force before the thread is stripped, even with bones of different strength.

While the preferred embodiment has been discussed, it should be recognized that variations can be made. It should be mentioned first of all that the screwdriver according to the invention can be used not only for tightening bone screws in tibiae but also for tightening screws in other bones. Also, screws with diameters other than 4.5 mm can, of course, be screwed on in similar fashion, and the screw heads do not have to have hexagonal sockets. The shank of the screwdriver obviously has to match the head of the screw to be tightened so that the end of the shank can engage positively in the screw head.

Furthermore, the screwdriver according to the invention can also be used in operations where implants, or plates, are to be screwed to the bone. In these cases the screw heads do not lie directly on the bone but on the plate. Since the friction is then rather different, the resistance of the potentiometer 25 or of the resistor 77 must, if necessary, be changed slightly.

The screwdriver illustrated in FIG. 1 has to be turned by hand for tightening a screw. The principle behind the invention can also be applied to a screwdriver having a shank which is arranged to rotate in a holder and which is powered by a pneumatic drive unit, for example. The two measuring transducers 21 and 23 would then naturally have to be modified accordingly. The torque would have to be measured, for example, between the shank and the shaft of the drive unit.

In addition, the level monitor and the signal generators can also be modified within broad limits. For example, two acoustic signal generators could be provided, one of which would generate a tone with a frequency proportional to the instantaneous torque value. The other signal generator could then generate a tone with a frequency proportional to the torque value $M_o$. From these two tones the surgeon would then be able to judge continuously how far below the optimum value the instantaneous torque still is.

In order to prevent any chance movements of the screw in the reverse direction from triggering any fault signals, the electronic section can be provided with a memory which stores the $M_o$ value determined until the end of the tightening process. Such fault signals can, however, also be prevented by appropriate design of the level monitor.

It would also be possible to equip the screwdriver with an electrically or pneumatically controllable clutch. If the shank of the screwdriver is rotated not by hand but by means of a drive unit, a controllable switching device could be provided for switching off the drive. The electronic section could then be connected with the controllable clutch or the controllable switching device respectively and control it in such a way that the shank is automatically disconnected or the shank drive switched off when the instantaneous torque M reaches the optimum torque value $M_o$.

It should also be mentioned that the value of the differential quotient $\partial M/\partial \alpha$ can, of course, also be found by determining the ratio $\Delta M/\Delta \alpha$ at any point on the approximately linear part of the curve. Thus the electronic section could be designed in such a way that it determines the difference quotient or the differential quotient when the torque has reached a given value of, for example, 0.7 Newton meters. The potentiometer 25 could then be replaced by a potentiometer in which the sliding contact can be rotated any number of times with the resistance starting at zero every time. If the device were so designed it would then no longer be necessary to set the potentiometer to zero when the screw head comes into contact with the bone.

Finally it ought to be said in addition that the optimum torque value $M_o$ can be related in yet another way to the differential quotient $\partial M/\partial \alpha$ or the difference quotient $\Delta M/\Delta \alpha$ or the ratio $M/\alpha$. The torque value $M_o$ defined should, however, also increase monotonically as the differential quotient $\partial M/\partial \alpha$ or the difference quotient $\Delta M/\Delta \alpha$ or the ratio $M/\alpha$ increases.

While specific embodiments of the present invention have been shown and described in the specification and drawings to illustrate and explain the present invention, it should be understood that the present invention is not limited to these specific embodiments, but contemplates other embodiments falling within the scope of the following claims.

I claim:

1. A bone screw driving device adapted for use in orthopedic and traumatologic surgery for tightening a bone screw into bone material to a value $M_O$ which is less, by a predetermined factor, than the torque value at which said bone material irreversibly deforms, said device comprising:
   i. a screw driving tool for engaging said bone screw to rotate and apply tightening torque to said bone screw;
   ii. means for measuring the amount of tightening torque applied to said bone screw by said screw driving means;
   iii. means for measuring the angle of rotation of said bone screw; and
   iv. control means for relating the tightening torque applied to said bone screw and the angle of rotation of said bone screw; for specifying a value for $M_0$ as a sum of at least one summand which is a constant, independent of torque, and a summand which is proportional to $M/\alpha$ where $\alpha$ is the angle of rotation of the screw measured from the contact of the screw head with an underlying surface, and M is the torque applied as the screw is rotated through $\alpha$; and for monitoring the applied tightening torque value for $M_0$.

2. The device claimed in claim 1 where $M_0$ also includes a summand proportional to the square of $M/\alpha$.

3. The device claimed in claim 2 wherein $M_0$ is defined as:

$$M_0 = C_0 + C_1 M/\alpha + C_2 (M/\alpha)^2$$

$C_0$, $C_1$ and $C_2$ being constants.

* * * * *